(12) United States Patent
Nieman

(10) Patent No.: US 8,137,260 B2
(45) Date of Patent: Mar. 20, 2012

(54) ELECTROMAGNETIC CARDIAC ASSIST DEVICE AND METHOD

(75) Inventor: Tim Nieman, Salt Lake City, UT (US)

(73) Assignee: Edwards Lifesciences Corporation, Irvine, CA (US)

( * ) Notice: Subject to any disclaimer, the term of this patent is extended or adjusted under 35 U.S.C. 154(b) by 415 days.

(21) Appl. No.: 12/468,228

(22) Filed: May 19, 2009

(65) Prior Publication Data

US 2009/0292160 A1    Nov. 26, 2009

Related U.S. Application Data

(60) Provisional application No. 61/055,406, filed on May 22, 2008.

(51) Int. Cl.
*A61N 1/362* (2006.01)
(52) U.S. Cl. .................................................. 600/16
(58) Field of Classification Search ............... 600/16, 600/17; 623/3, 3.11, 3.27, 3.28
See application file for complete search history.

(56) References Cited

U.S. PATENT DOCUMENTS

| 4,621,617 | A | * | 11/1986 | Sharma | 600/16 |
| 6,099,460 | A | * | 8/2000 | Denker | 600/17 |
| 6,123,724 | A | * | 9/2000 | Denker | 623/3.11 |
| 6,309,341 | B1 | * | 10/2001 | Denker | 600/16 |
| 6,604,529 | B2 | * | 8/2003 | Kim | 128/899 |

* cited by examiner

*Primary Examiner* — Brian T Gedeon
(74) *Attorney, Agent, or Firm* — Melinda R. Michalerya

(57) ABSTRACT

Embodiments of the present invention provide systems and methods for assisting with contraction of the heart muscle. For example, in one embodiment of the invention, one or more flexible strips are attached to the surface of the heart, each strip having a plurality of electromagnets alternating with a plurality of permanent magnets. The electromagnets are electrically coupled to a control device and a power supply for generating current in the electromagnets. The control device controls the current in the electromagnets in such a way that the electromagnets are periodically activated to attract the adjacent permanent magnets to assist with contraction of the heart muscle. In some embodiments a sensor is provided for sensing the sinus rhythm so that the control device can activate the electromagnets based on the sensed sinus rhythm.

7 Claims, 3 Drawing Sheets

ELECTROMAGNETIC CARDIAC ASSIST DEVICE AND METHOD

CLAIM OF PRIORITY UNDER 35 U.S.C. §119

The present Application for patent claims priority to Provisional Application No. 61/055,406 filed May 22, 2008, and assigned to the assignee hereof and hereby expressly incorporated by reference herein.

FIELD

The invention generally relates to the field of circulatory support devices, and more particularly, embodiments of the present invention relate to using one or more magnets to assist with contraction of a heart muscle.

BACKGROUND

Congestive heart failure is a condition in which the heart is unable to pump enough blood to the body's other organs. The New York Heart Association (NYHA) Functional Classification provides a way to classify heart failure patients based on how much the patient is limited during physical activity. For example, Class 1 patients suffer no symptoms from ordinary activities; Class 2 patients experience a slight, mild limitation of activity and are comfortable with rest or with mild exertion; Class 3 patients experience a marled limitation of activity and are comfortable only at rest; and Class 4 patients should be at complete rest, confined to bed or chair, and symptoms occur even at rest.

Congestive heart failure patients are initially treated during NYHA Classes 1-3 stages of this degenerative disease. For patients that do not respond to these treatments and degrade to Class 4, ventricular assist devices (VADs) are often utilized as a last resort either as a bridge to heart transplant surgery or, in most critically ill patients who are ineligible for transplant, as a destination therapy. The VADs typically consist of displacement, centrifugal, or axial-flow blood pumps. These devices are often thought of as a last resort because the pumps currently have a limited life, typically on the order of 2-3 years. Following that time period, the device must be replaced. Although many companies are developing longer life products, these do not yet currently exist.

A secondary complication for these VADs is that blood must be routed from the patient's heart to the pump and then returned to the arterial supply via an aortic cannula. Since this requires blood flow through one or more man-made devices, a significant concern is clotting, pannus formation within the cannula, and complications from medications used to counter thrombus formation. Currently, no pump exists that allows a patient freedom from anticoagulation medications and the side effects thereof. Additionally, since blood must pass through the pump, the blood is often passing over bearings or within channels that both present thrombus and hemolytic concerns.

Yet another complication with VADs is that a proper balance between flow rates and patient activity must be maintained. Specifically, in order to provide the patient benefit, the pump must provide the necessary flow rate while still allowing the aortic valve to open and close to prevent thrombus formation and stroke potential. The pump must accomplish all this within the various ranges of patient activities. Typically, with current VADs, a patient provides this control by selecting from a series of pump settings.

In summary, VADs are a last resort because use of VADs involves numerous complications due to associated medications, thrombotic and hemolytic concerns, and the effective life of the current VADs. As such, VADs do not provide effective therapies for those heart failure patients between NYHA Class 1 and end-stage Class 4.

BRIEF SUMMARY OF EMBODIMENTS OF THE INVENTION

Embodiments of the present invention provide a cardiac assist device and procedure for assisting with the heart's beating motion. For example, in one embodiment of the invention, one or more flexible strips are attached to the surface of the heart, each strip having a plurality of electromagnets alternating with a plurality of permanent magnets. The electromagnets are electrically coupled to a control device and a power supply for generating current in the electromagnets. The control device controls the current in the electromagnets in such a way that the electromagnets are periodically activated to attract the adjacent permanent magnets to assist with contraction of the heart muscle. In some embodiments a sensor is provided for sensing the sinus rhythm so that the control device can activate the electromagnets based on the sensed sinus rhythm. In some embodiments, the cardiac assist device is configured to be placed on the heart in such a way as to provide the additional blood flow needed by NYHA Class 1-4 patients without requiring anti-coagulation therapy or blood access.

More particularly, embodiments of the present invention provide a cardiac assist device comprising a first electromagnet configured to be attached to a first location on a heart, and a second magnet or magnetic material member configured to be attached to a second location on the heart. The cardiac assist device also includes a power supply for generating current in the first electromagnet, where the power supply is electrically coupled to the first electromagnet. In general, the first electromagnet is configured such that using the power supply to generate current in the first electromagnet in a first direction creates a magnetic field that attracts the second magnet or magnetic material member to the first electromagnet. As a result, the cardiac assist device creates a force configured to pull the first location of the heart towards the second location of the heart.

In one embodiment, the second magnet or magnetic material member of the cardiac assist device is a second electromagnet. In such embodiments, where the first electromagnet comprises a first electromagnet coil defining a first longitudinal axis therethrough and the second electromagnet comprises a second electromagnet coil defining a second longitudinal axis therethrough, the first longitudinal axis is substantially aligned with the second longitudinal axis.

In other embodiments of the invention, the second magnet or magnetic material member of the cardiac assist device is a permanent magnet. In still other embodiments, the second magnet or magnetic material member is a paramagnetic or ferromagnetic material member.

The cardiac assist device further includes a control device communicatively coupled to the first electromagnet and the power supply. The control device is configured to control the current in the first electromagnet. For example, in one embodiment the control device is configured to repeatedly alternate between applying current in the first electromagnet in a first direction and not applying current in the first electromagnet in the first direction.

The cardiac assist device generally also includes a flexible substrate on which the first electromagnet and the second magnet or magnetic material member are both attached. The flexible substrate is configured to be attached to the heart by, for example sutures, surgical adhesives, or other mechanisms.

In one embodiment, the cardiac assist device has a flexible substrate configured to be attached to the heart and at least a third magnet or magnetic material member. In one such embodiment, all of the at least three magnets or magnetic material members are attached to the flexible substrate in a generally linear relationship such that the electromagnet(s) alternate with the permanent magnet(s) or other magnetic material member(s). In some embodiments where the three magnets or magnetic material members are magnets, the first, second, and third magnets are attached to the flexible substrate in a generally linear relationship such that the polarities of each of the three magnets are aligned. In this way, adjacent magnets on the flexible substrate attract each other at least when current is running through any electromagnets on the flexible substrate.

In some embodiments, the cardiac assist device includes a control device communicatively coupled to the first electromagnet and the power supply and configured to reverse the current in the first electromagnet in order to reverse the polarity of the first electromagnet. In this way, the first electromagnet can be made to repel the second magnet or magnetic material member, thereby, creating a force configured to push the first location of the heart away from the second location of the heart. For example, in one embodiment the control device briefly reverses the polarity after contraction to assist the heart with re-expansion.

The cardiac assist device has, in some embodiments, a flexible sheet or mesh configured to be attached to the heart, as well as at least a third magnet. In one such embodiment, the first, second, and third magnets are attached to the flexible sheet or mesh in a two-dimensional arrangement such that cardiac assist device assists the heart with contractions in at least two dimensions.

In some embodiments, the cardiac assist device includes a sensor communicatively coupled to the control device. For example, in one embodiment such a sensor is configured to sense the sinus rhythm and to communicate a signal to the control device based on the sensed rhythm. The control device is configured to control the first electromagnet based on the signal received from the sensor. In some embodiments, the control device is positioned subcutaneously.

Embodiments of the present invention also provide a device for assisting with the contraction and/or expansion of tissue, such as the heart, sphincter, esophagus, or other muscle. The device generally includes a flexible substrate for attaching to the tissue. The device also includes at least two magnetic members attached to the substrate. At least one of the two magnetic members comprises an electromagnet. The device also typically includes a power supply configured to generate a current in the electromagnet and a control device electrically coupled to the power supply and the electromagnet for controlling the current in the electromagnet.

The device includes, in some embodiments, at least three magnetic members attached to the substrate. The at least three magnetic members are attached in a generally linear relationship and at least one of the three magnetic members comprises an electromagnet. In some embodiments, the at least three magnetic members comprise two permanent magnets with the electromagnet located between the two permanent magnets. In other embodiments, the at least three magnetic members comprise two ferromagnetic or paramagnetic material members with the electromagnet located between the two magnetic material members. In still other embodiments, the at least three magnetic members comprise a second electromagnet and a permanent magnet, with the permanent magnet located between the two electromagnets. In still other embodiments, the at least three magnetic members comprise a second electromagnet and a ferromagnetic or paramagnetic material member, with the ferromagnetic or paramagnetic material member located between the two electromagnets.

In some embodiments of the device, the flexible substrate comprises a flexible sheet or mesh, and the at least three magnets are attached to the flexible sheet or mesh in a two-dimensional arrangement. In other embodiments, the flexible substrate comprises an elongate strip of flexible fabric.

Embodiments of the present invention also provide a method for assisting cardiac function. The method generally includes: (1) attaching an electromagnet to a first location on a heart; (2) attaching a second magnet or magnetic material member to a second location on the heart; (3) attaching the electromagnet to a power supply; and (4) configuring a control device to control the current through the electromagnet so that the electromagnet periodically attracts the second magnet or magnetic material member to assist at least a portion of the heart with contraction.

In some embodiments, attaching an electromagnet to a first location and attaching a second magnet or magnetic material member to a second location involves attaching a plurality of flexible strips to the surface of the heart. Each flexible strip includes at least a first electromagnet and at least a second magnet or magnetic material member attached thereto.

In some embodiments, the method further includes attaching a sensor to a portion of the body to sense the sinus rhythm, and configuring the controller to receive an indication of the sensed rhythm and to control the current through the electromagnet based on the received indication of the sensed rhythm.

In some embodiments, the method involves attaching the magnets to a beating heart. The method also is, in some instances, practiced using minimally invasive procedures, such as port-access procedures.

BRIEF DESCRIPTION OF THE SEVERAL VIEWS OF THE DRAWINGS

Figure 1:
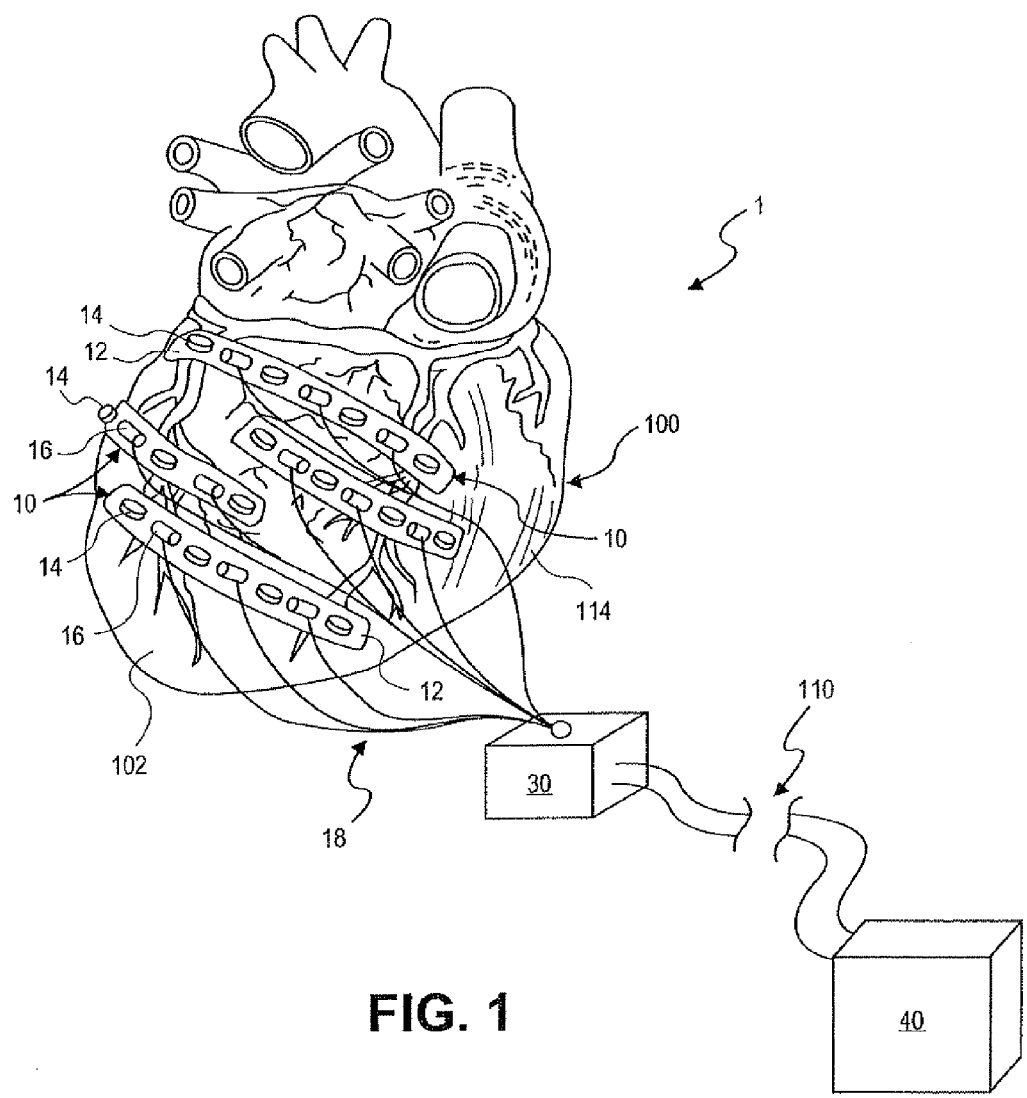
Figure 2:
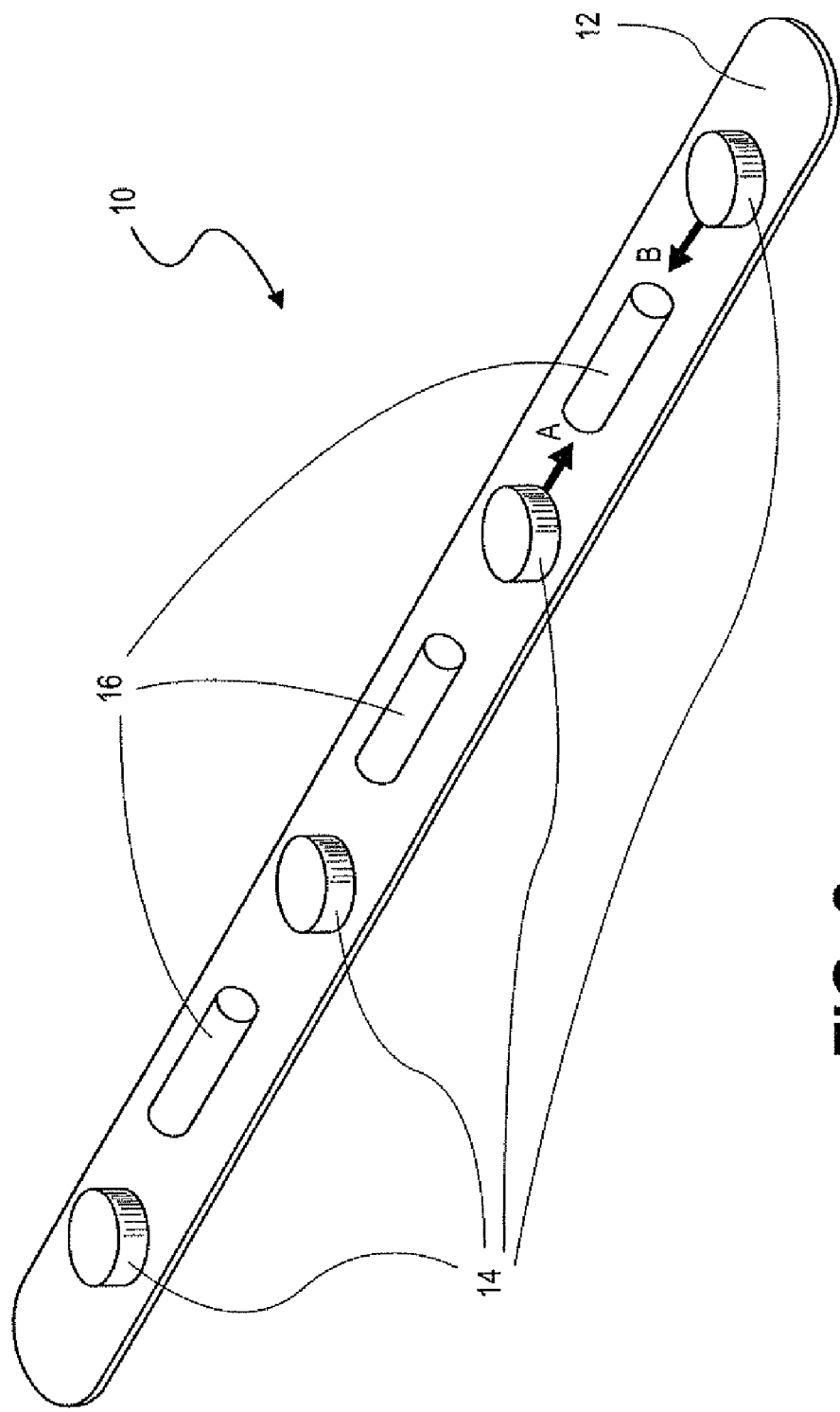
Figure 3A:
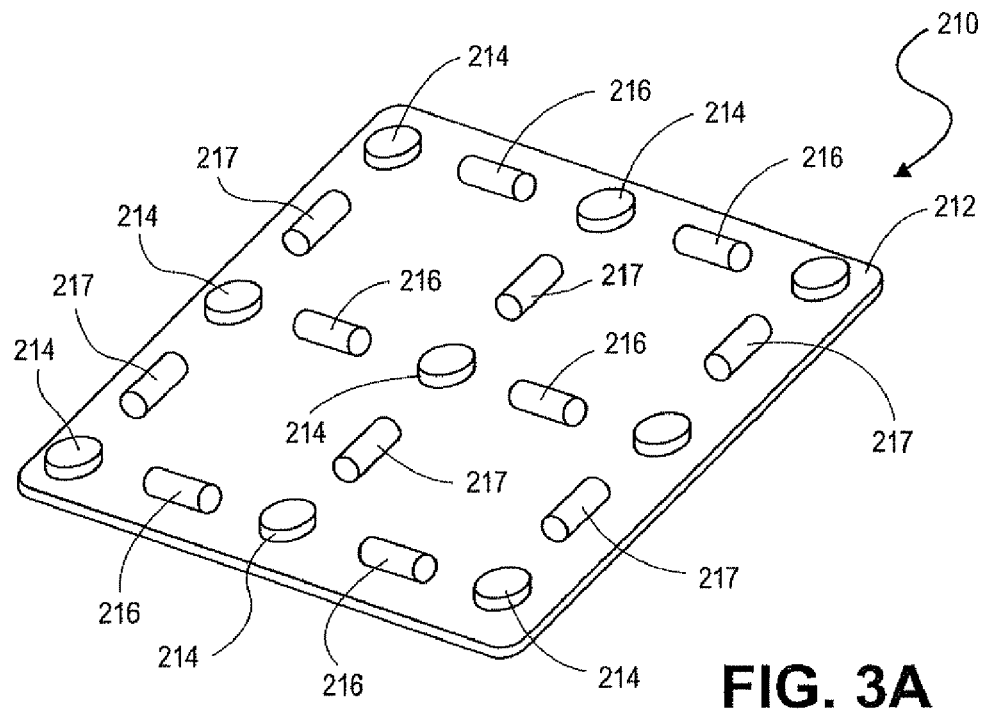
Figure 3B:
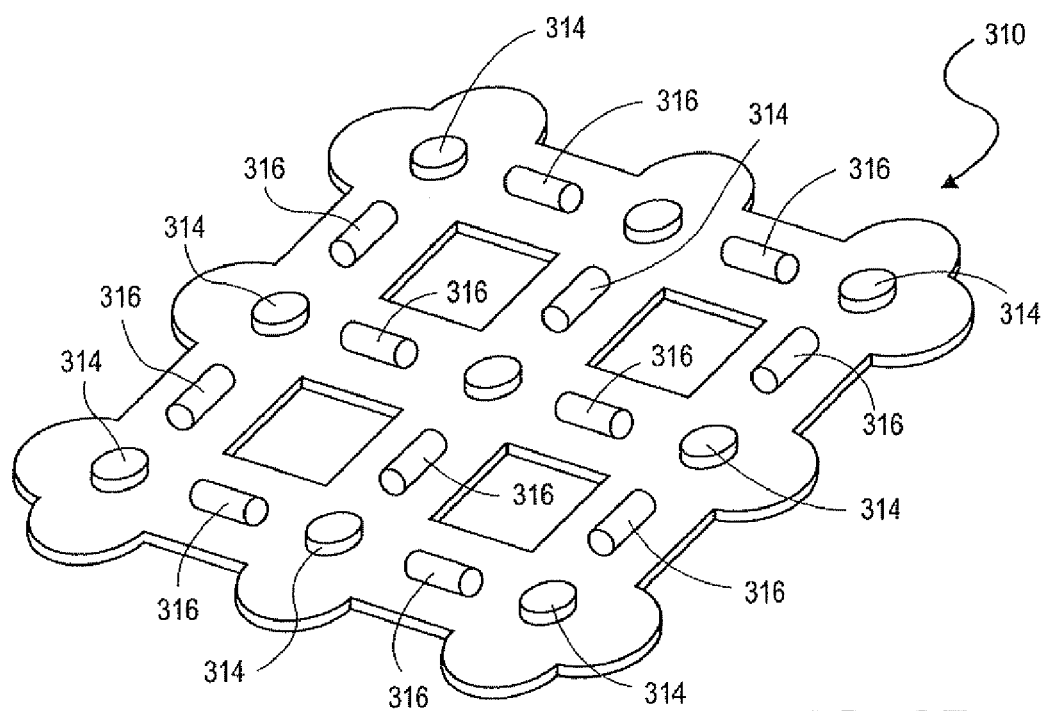

Having thus described embodiments of the invention in general terms, reference will now be made to the accompanying drawings, which are not necessarily draw to scale, and wherein:

FIG. 1 illustrates a cardiac assist device in accordance with an embodiment of the present invention;

FIG. 2 illustrates a magnet strip used in the cardiac assist device of FIG. 1, in accordance with an embodiment of the present invention; and FIGS. 3a and 3b illustrate magnet sheets for use in a cardiac assist device in accordance with other embodiments of the present invention.

DETAILED DESCRIPTION OF EMBODIMENTS OF THE INVENTION

Embodiments of the present invention now will be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout. As used herein, the term "magnet," when used alone, may refer to an electromagnet, a permanent magnet, and/or any other type of magnet.

FIG. 1 illustrates a cardiac assist device 1 in accordance with an embodiment of the present invention. In the illustrated embodiment, the cardiac assist device 1 includes a plurality of magnet "strips" 10 attached to the heart 100 to assist at least portions of the heart 100 with contractile motion. FIG. 2 illustrates a magnet strip 10 used in the embodiment of the cardiac assist device 1 illustrated in FIG. 1. In some embodiments of the present invention, the cardiac assist device 1 "assists" the heart 100 by augmenting the natural contraction of myocardial tissue. However, in other embodiments of the present invention, the cardiac assist device 1 "assists" the heart 100 by creating pseudo-contractile motion in ischemic, necrotic, scarred, or otherwise non-functioning myocardial tissue.

As illustrated in FIGS. 1 and 2, in an exemplary embodiment, each magnet strip 10 includes a plurality of magnets attached to a substrate 12 in a generally linear relationship. In particular, in the illustrated embodiment, each strip 10 has four permanent magnets 14 (one permanent magnet located proximate to each end of the strip 10 and two additional permanent magnets spaced equidistant between the permanent magnets at each end). One of three electromagnet coils 16 is positioned between each adjacent pair of permanent magnets 14 such that the magnets on the strip 10 are arranged to alternate between permanent magnets 14 and electromagnets 16. In one embodiment, the permanent magnets 14 are spaced sufficiently far apart on the strip 10 such that they do not significantly attract each other when the strip 10 is laid-out in its natural, un-contracted, state.

Electrical leads 18 couple each end of each electromagnet coil 16 to a control device 30. In one embodiment, the control device 30 is configured to electrically couple and decouple the electrical leads 18 to a power supply 40, such as a battery. When the control device 30 electrically couples the electrical leads 18 to the power supply 40, the power supply 40 generates an electrical current in the electromagnet coils 16. As a result, each electromagnet coil 16 becomes an electromagnet. In one embodiment, the control device 30 is also configured to adjust the magnitude of the current flowing through some or all of the electromagnet coils 16 to control the intensity of the electromagnetic fields surrounding the electromagnet coils 16. For example, in one embodiment the control device 30 includes a variable resistor connected in series with one or more of the electromagnets 16 and the power supply 40. The control device 30 is then configured to use the resistor to control the current flowing through the electromagnet(s) 16.

In some embodiments, instead of the control device 30 decoupling the electromagnet coils 16 from the power supply 40, the electromagnet coils 16 remain electrically coupled to the power supply 40 throughout the contraction and expansion of the heart 100. In such embodiments, when the heart muscle is supposed to relax after a contraction, the control device 30 significantly reduces the magnitude of the current in the electromagnets 16 to a point that the attraction between the magnets becomes insignificant.

In one embodiment, the control device 30 is located within the patient's body, under the patient's skin 110, while the power supply 40 is located outside the patient's body. In other embodiments, both the control device 30 and the power supply 40 are located within the patient's body or outside of the patient's body. In still other embodiments, a portion of the control device 30 is located within the patient's body and another portion of the control device 30 is located outside the patient's body.

The direction of the current generated in an electromagnet coil 16 determines which end of the coil 16 is the "north" pole and which is the "south" pole of the resulting magnet. In the illustrated embodiment, the magnets are aligned on the substrate 12 and connected to the power supply 40 in such a way that, when the electromagnet coils 16 are electrified, each electromagnet 16 creates a magnetic field that works to pull the permanent magnets 14 on each side of the electromagnet 16 toward the electromagnet 16, as illustrated by the arrows A and B in FIG. 2. In this way, when the strip 10 is attached to the heart 100, activation of the electromagnets 16 forces or helps the heart muscle to contract.

In general, the electromagnet coil 16 comprises a wire that is coiled to form a solenoid, where the solenoid defines a longitudinal axis through the center of the solenoid. In such an embodiment, the electromagnet coils 16 are positioned such that the longitudinal axes of the coils 16 are generally in alignment with each other on the strip 10. Furthermore, at least in the illustrated embodiment, when it is desired for all of the magnets in the strip 10 to be attracted towards each other, the electrical leads 18 are electrically connected to the power supply such that current is passed through each electromagnet coil 16 in the same direction. In some embodiments, each electromagnet 16 includes a "core" of paramagnetic or ferromagnetic material, such as soft iron, placed inside the coil along the longitudinal axis of the coil. Such a core can be used to concentrate the magnetic field to create a stronger attraction between each electromagnet 16 and the adjacent magnets on the strip 10.

Since the substrate 12 must allow the magnets to move toward each other, the substrate 12 is typically made of a material that is flexible, at least in the axial contractile direction. In this regard, the substrate 12 and the technique used to attach the substrate 12 to the heart 100 are preferably selected such that they do not make it significantly more difficult for the heart wall 100 to contract when the magnets are not activated.

Although the substrate 12 must allow for contraction, the substrate 12, in one embodiment, is configured such that it is unable to expand significantly in the axial direction Furthermore, in one embodiment, the substrate 12 is made of materials that will tend to incorporate tissue. In this way, in some embodiments, the strips 10 function as a heart "truss" for resisting ventricular dilation of the heart 100. In one exemplary embodiment, the substrate 12 is made of a strip of fabric, such as a six-inch strip of Dacron® vascular graft material or other polymeric fabric. In other embodiments of the present invention, however, the strip 10 is able to stretch in the axial direction.

In one embodiment, the magnet strips 10 are attached epicardially to the surface of a beating heart 100, such as to the heart's myocardium. However, in other embodiments, the magnet strips 10 are placed extra-pericardially on the heart 100. For example, in some instances, the magnet strips 10 are sewn through the pericardium to the myocardium to eliminate adhesions between the thoracic cavity and the epicardium. This may allow for reduced complications in the event of a need for other procedures. The magnet strips 10 may be attached to the heart 100 using sutures, staples, adhesives, friction, tissue incorporation, or any other attachment mechanism that one of ordinary skill in the art would recognize as appropriate in view of this disclosure. In some embodiments, the cardiac assist device 1 is placed within the body using a subxiphoid or minimally-invasive procedure.

As illustrated in FIG. 1, more than one magnet strip 10 may be attached to the heart 100. Where multiple magnet strips 10 are used, the magnetic strips are positioned generally parallel to each other, as shown in FIG. 1, or in various other configurations and formations. FIG. 1 illustrates using magnet strips 10 on the left ventricle 102 of the heart 100. However, in other embodiments, the magnet strips 10 are placed on the right ventricle 114 or other portions of the heart 100 in addition to or as an alternative to placing magnet strips 10 on the left ventricle 102. In one embodiment, one or more strips 10 completely surround a portion of the heart 100.

In some embodiments, the control device 30 activates all of the electromagnets 16 on all of the magnet strips 10 simultaneously. In other embodiments, however, the control device 30 activates the electromagnets 16 across a magnet strip 10, or on different magnet strips 10, at slightly different times. For example, it may be desirous to activate the electromagnets 16 at slightly different times where magnet strips 10 cover different areas of the heart 100 that are supposed to contract at slightly different times or rates. In some embodiments, the control device 30 also causes different electromagnets 16 to have different magnetic intensities by controlling the current through the different electromagnet coils 16. This may be advantageous if some areas of the myocardium are supposed to contract further or faster than other areas of the myocardium.

In some embodiments of the present invention, the cardiac assist device 1 includes one or more sensors (not shown) communicatively coupled to the control device 30 for use in pacing the activation of the electromagnets 16. In one embodiment, where the cardiac assist device 1 is intended to augment rather than replace the heart's natural contractions, the sensor(s) is/are configured to sense the sinus rhythm and activate the electromagnet coils 16 during, for example, ventricular systole (or systole of some other portion of the heart where the magnet strips 10 are positioned). Such sensor(s) may be positioned within the patient's body or externally. The sensor(s) may communicate with the control device 30 using wired or wireless mechanisms. In some embodiments, in addition to or as an alternative to using the sensor(s) to sense sinus rhythm, the control device 30 uses the sensor(s) to monitor the patient or the cardiac assist device's performance. For example, in one embodiment the control device 30 continuously records an electrocardiogram (ECG) for the patient.

As will be apparent to one or ordinary skill in the art, in order to perform some of the functions described above, the control device 30 typically includes one or more memory devices and/or processing devices. The control device 30 also typically includes one or more input devices in addition to or as an alternative to the sensor(s) described above. For example, in one embodiment the control device 30 includes a user input device for adjusting the rate or intensity of the electromagnet activation. In some embodiments the control device 30 also includes one or more output devices for providing information to a user, such as information about whether the cardiac assist device 1 is functioning properly, or warning signals when the control device 30 senses something abnormal. In some embodiments the control device 30 also includes one or more output devices for providing information, such as a recorded ECG, to one or more external devices. In this regard, the control device 30 may be configured to communicate with other devices using wired or wireless systems, such as radio-frequency systems.

As described above, in some embodiments of the invention the magnet strips 10 have alternating electromagnets 16 and permanent magnets 14. In other embodiments of the invention, however, the permanent magnets 14 are replaced with other magnetic materials that are not necessarily "permanent" magnets themselves. In still other embodiments, electromagnets 16 are placed on a magnetic strip 10 adjacent to other electromagnets 16 instead of permanent magnets 14 such that the two adjacent electromagnets attract each other when current is flowing through the electromagnets in the same direction.

Although FIGS. 1 and 2 illustrate an embodiment of the invention where a magnet strip 10 includes four permanent magnets 14 and three electromagnets 16, in other embodiments of the invention the magnet strip 10 includes any number of permanent magnets 14 and/or electromagnets 16. In one embodiment, long magnet strips are provided to a user that allow the user to cut the long magnet strip into smaller strips depending on the size needed for the user's particular application. In some embodiments, individual magnets are each attached to their own separate substrate so that a user can separately sew or otherwise attach each individual magnet to the heart adjacent to one or more other individual magnets such that the two or more adjacent individual magnets will attract when current flows through one or more of the magnets.

Furthermore, although FIGS. 1 and 2 illustrate magnet "strips" 10 having magnets aligned thereon in a generally linear relationship, other embodiments of the present invention provide magnets arranged two-dimensionally on a substrate, or otherwise attached on the surface of the heart 100, in such a way as to cause contraction or expansion of the heart muscle in two or more dimensions. For example, FIGS. 3a and 3b illustrate two exemplary embodiments of magnet "sheets" 210 and 310 for use in a cardiac assist device 1 in accordance with other embodiments of the present invention. As illustrated in FIGS. 3a and 3b, a sheet-like substrate 212/312 is provided having multiple magnets arranged thereon configured to contract the substrate in more than one dimension when current is applied to the electromagnets.

For example, in the exemplary embodiments illustrated in FIGS. 3a and 3b, a first set of electromagnets 216/316 are attached to the substrate 212/312 such that the longitudinal axis defined by the electromagnet coils are aligned in a first direction. A second set of electromagnets 217/317 are attached to the substrate 212/312 such that the longitudinal axis defined by the electromagnet coils are aligned in a second direction different than the first direction. For example, as illustrated in FIGS. 3a and 3b, the first and second sets of electromagnets can be aligned perpendicularly to each other. In the illustrated embodiments, pieces of other magnetic material 214/314, such as pieces of ferromagnetic material or permanent magnets, are attached to the substrate between the electromagnets as shown. FIG. 3b illustrates an embodiment of a magnet sheet 310 where the substrate 312 has a mesh or lattice-like configuration that may more easily contract in two dimensions compared to the solid sheet illustrated in FIG. 3a.

The embodiments described herein are generally described has being configured such that all of the magnets of the cardiac assist device 1 attract adjacent magnets when current flows through the electromagnets 16. However, in some embodiments, the direction of the current in some or all of the electromagnets 16 is reversed so that two or more adjacent magnets repel each other. In this way, embodiments of the present invention can also be used to expand tissue in a patient's body. For example, in one embodiment, the control device 30, after activating the electromagnets 16 to assist with contraction of the heart 100, briefly switches the polarity of some or all of the electromagnets 16 so that the cardiac assist device 1 also assists with expansion of the heart 100 during the heart's beating motion.

In some embodiments, some of the magnets on a magnet strip or sheet are configured to attract adjacent magnets while other magnets on the strip or sheet are configured to repel adjacent magnets. Such an embodiment may be useful where it is desirous to contract only portions of the heart 100.

Although the embodiments of the present invention described herein are generally described as being configured to assist with the contraction and/or expansion of the heart 100, other embodiments of the present invention can be used to assist with the contraction and/or expansion of other body tissues, such as other muscles or organs. For example, in one embodiment, embodiments of the magnet strips are secured to the sphincter muscle to assist with contraction of the sphincter and help cure incontinence. In another example, embodiments of the magnet strips are implanted on or around the esophagus, stomach, intestines, or other portions of the digestive tract to assist with peristalsis or other muscle contractions and/or relaxations.

In one embodiment, the cardiac assist device 1 is attached to the heart 100 while the heart 100 is beating. Such a procedure may be advantageous since it would not involve the added complications sometimes involved with cardiopulmonary bypass procedures. Furthermore, in some instances, the surgeon uses minimally invasive procedures to attach the magnets or the magnet strips or sheets to the surface of the heart 100. For example, in one embodiment the surgeon accesses the patient's thoracic cavity through an incision in an intercostal space. The surgeon then uses specially-configured minimally invasive tools to carry the magnets or magnet strips or sheets to the heart 100 and to sew or otherwise attach the magnets to the heart 100.

It should also be appreciated that embodiments of the present invention provide a system and method for assisting with the heart's pumping functions in such a way that, in at least some embodiments of the invention, the patient's natural vessels are maintained and the need for anticoagulation medications is reduced or eliminated.

Specific embodiments of the invention are described herein. Many modifications and other embodiments of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments and combinations of embodiments are intended to be included within the scope of the appended claims. Although specific terms are employed herein, they are used in a generic and descriptive sense only and not for purposes of limitation.

What is claimed is:

1. A cardiac assist device comprising:
a first electromagnet configured to be attached to a first location on a heart;
a second magnet or magnetic material member configured to be attached to a second location on the heart; and
a power supply for generating current in the first electromagnet, the power supply electrically coupled to the first electromagnet, wherein the first electromagnet is configured such that using the power supply to generate current in the first electromagnet in a first direction creates a magnetic field that attracts the second magnet or magnetic material member to the first electromagnet, thereby, creating a force configured to pull the first location of the heart towards the second location of the heart and wherein the second magnet or magnetic material member comprises a paramagnetic or ferromagnetic material member.

2. A cardiac assist device comprising:
a first electromagnet configured to be attached to a first location on a heart;
a second magnet or magnetic material member configured to be attached to a second location on the heart;
a power supply for generating current in the first electromagnet, the power supply electrically coupled to the first electromagnet, wherein the first electromagnet is configured such that using the power supply to generate current in the first electromagnet in a first direction creates a magnetic field that attracts the second magnet or magnetic material member to the first electromagnet, thereby, creating a force configured to pull the first location of the heart towards the second location of the heart;
a flexible substrate configured to be attached to the heart; and
at least a third magnet or magnetic material member, wherein the at least three magnets or magnetic material members are attached to the flexible substrate in a generally linear relationship such that the electromagnet(s) alternate with permanent magnet(s) or other magnetic material member(s).

3. A cardiac assist device comprising:
a first electromagnet configured to be attached to a first location on a heart;
a second magnet or magnetic material member configured to be attached to a second location on the heart;
a power supply for generating current in the first electromagnet, the power supply electrically coupled to the first electromagnet, wherein the first electromagnet is configured such that using the power supply to generate current in the first electromagnet in a first direction creates a magnetic field that attracts the second magnet or magnetic material member to the first electromagnet, thereby, creating a force configured to pull the first location of the heart towards the second location of the heart;
a flexible substrate configured to be attached to the heart; and
a third magnet, wherein the second magnet or magnetic material member comprises a magnet, wherein the first, second, and third magnets are attached to the flexible substrate in a generally linear relationship such that the polarities of each of the three magnets are aligned in such a way that adjacent magnets on the flexible substrate attract each other at least when current is running through any electromagnets on the flexible substrate.

4. A device for assisting with the contraction or expansion of tissue, the device comprising:
a flexible substrate for attaching to the tissue;
a power supply configured to generate a current in an electromagnet;
a control device electrically coupled to the power supply and the electromagnet for controlling the current in the electromagnet;
at least three magnetic members attached to the substrate in a generally linear relationship, wherein at least one of the three magnetic members comprises an electromagnet; and
wherein the at least three magnetic members further comprise two permanent magnets, and wherein the electromagnet is located between the two permanent magnets.

5. The device of claim 4, wherein the at least three magnetic members further comprise two ferromagnetic or paramagnetic material members, and wherein the electromagnet is located between the two magnetic material members.

6. The device of claim 4, wherein the at least three magnetic members further comprise a second electromagnet and a permanent magnet, and wherein the permanent magnet is located between the two electromagnets.

7. The device of claim 4, wherein the at least three magnetic members further comprise a second electromagnet and a ferromagnetic or paramagnetic material member, and wherein the ferromagnetic or paramagnetic material member is located between the two electromagnets.

* * * * *